(12) United States Patent
Sato (10) Patent No.: US 8,222,399 B2
(45) Date of Patent: Jul. 17, 2012

(54) PHOTOREACTIVE POLYSACCHARIDE, PHOTOCROSSLINKED POLYSACCHARIDE PRODUCT AND METHOD OF MAKING SAME AND MEDICAL MATERIALS MADE FROM THE CROSSLINKED POLYSACCHARIDE

(75) Inventor: Tomoya Sato, Higashiyamato (JP)

(73) Assignee: Seikagaku Corporation (JP)

( * ) Notice: Subject to any disclaimer, the term of this patent is extended or adjusted under 35 U.S.C. 154(b) by 1648 days.

(21) Appl. No.: 11/162,597

(22) Filed: Sep. 15, 2005

(65) Prior Publication Data

US 2006/0057098 A1 Mar. 16, 2006

(30) Foreign Application Priority Data

Sep. 15, 2004 (JP) ................................ 2004-268145

(51) Int. Cl.
- C08B 37/08 (2006.01)
- A61K 31/728 (2006.01)
- C12N 5/02 (2006.01)

(52) U.S. Cl. ............................. 536/53; 514/54; 435/395
(58) Field of Classification Search .................... 536/53; 514/54

See application file for complete search history.

(56) References Cited

U.S. PATENT DOCUMENTS

| | | | |
|---|---|---|---|
| 4,115,332 A * | 9/1978 | Young et al. | ............. 526/238.22 |
| 4,564,560 A * | 1/1986 | Tani et al. | .................. 428/32.26 |
| 5,462,976 A | 10/1995 | Matsuda et al. | |
| 5,763,504 A | 6/1998 | Matsuda et al. | |
| 6,025,444 A | 2/2000 | Waki et al. | |
| 6,031,017 A | 2/2000 | Waki et al. | |
| 6,107,410 A | 8/2000 | Waki et al. | |
| 6,586,493 B1 | 7/2003 | Massia et al. | |
| 6,602,859 B2 | 8/2003 | Miyamoto et al. | |
| 2003/0031697 A1* | 2/2003 | Chudzik et al. | ............... 424/423 |

FOREIGN PATENT DOCUMENTS

| | | |
|---|---|---|
| JP | 56147802 A | 11/1981 |
| JP | 11-228639 A | 8/1999 |
| WO | WO 02060971 A1 | 8/2002 |
| WO | WO 200526214 A1 | 3/2005 |

OTHER PUBLICATIONS van Dijk-Wolthuis et al. Macromolecules, 1997, 30, p. 3411-3413.*
Trudel et al. Biomaterials, 2002, 23, p. 3299-3307.*
Frings et al. DIC Technical Review, 2003, No. 9, p. 43-51, http://www.dic.co.jp/en/research/technical/2003.html, accessed online Aug. 19, 2003.*
Jensen et al. entitled "Loading Into the Electro-Stimulated Release of Peptides and Proteins from Chondroitin 4-Sulphate Hydrogels," European Journal of Pharmaceutical. Sciences 15 (2002) pp. 139-148.
Li, et al., Photocrosslinkable Polysaccharides based on Chondroitin Sulfate, Journal of Biomedical Materials Research, Wiley NY, vol. 68, No. 1, Jan. 2004, pp. 28-33.
Leach, et al., Photocrosslinked Hyaluronic Acid Hydrogels: Natural, Biodegradable Tissue Engineering Scaffolds, Biotechnology and Bioengineering, Wiley, NY, vol. 82, No. 5, Jun. 2003, pp. 578-589.
English translation of Sep. 27, 2011 Office Action issued for related Japanese Application (No. 2005-263042).

* cited by examiner

Primary Examiner — Shaojia Anna Jiang
Assistant Examiner — Jonathan S Lau
(74) Attorney, Agent, or Firm — Factor Intellectual Property Law Group, Ltd.

(57) ABSTRACT

A photoreactive polysaccharide which comprises a polysaccharide bound to a glycidyl ester via a covalent bond, a photocrosslinked-polysaccharide prepared by using the photoreactive polysaccharide, and medical products comprising the photocrosslinked-polysaccharide.

15 Claims, 2 Drawing Sheets

Fig. 1

Fig. 2

PHOTOREACTIVE POLYSACCHARIDE, PHOTOCROSSLINKED POLYSACCHARIDE PRODUCT AND METHOD OF MAKING SAME AND MEDICAL MATERIALS MADE FROM THE CROSSLINKED POLYSACCHARIDE

CROSS-REFERENCE TO RELATED APPLICATIONS

This application is a continuation-in-part of Japanese Application No. 2004-268145, filed Sep. 15, 2004, and relies on the priority thereof.

TECHNICAL FIELD

The present invention relates to a photoreactive polysaccharide, a photocrosslinked-polysaccharide product produced by photocrosslinking a photoreactive polysaccharide, and medical products made from the crosslinked compound. More particularly, the present invention relates to a polysaccharide bound to a glycidyl ester which has a carboxyl group and an unsaturated carbon double bond to facilitate photoreactivity and crosslinking, a photocrosslinked-polysaccharide product produced by irradiating the polysaccharide with light, and a medical product comprising the photocrosslinked-polysaccharide.

BACKGROUND OF THE INVENTION

Since a polysaccharide is a safe polymer derived from the living body, application of modified substances of the polysaccharide to various medical materials has been attempted.

An example of such a medical products disclosed in *Eur. J. Pharm. Sci.*, 2002 March; 15(2): 139-48, where a polysaccharide gel is made by crosslinking chondroitin sulfate using a diglycidyl ether as a crosslinking agent. In this type of process, the crosslinking reaction takes place together with the reaction of chondroitin sulfate with the crosslinking agent. It has been found that it is difficult to remove the unreacted crosslinking agent from the crosslinked-gel after completion of the reactions. This deficiency may cause problems as it has been confirmed by experiments that disorder happens in the liver when a sponge-formed or gel-formed crosslinked-polysaccharide in which the crosslinking agent is insufficiently removed is applied, for example, into the abdominal cavity as an antiadhesive agent. Accordingly, removal of a crosslinking agent is important. When a crosslinked-polysaccharide is spongy, removal by washing is relatively easy but, when it is in the form of gel or film, the crosslinking agent is incorporated into the inner area whereby its removal is very difficult.

In view of the above, it has been proposed to synthesize a polysaccharide which is photoreactive. In particular, it has been proposed as a preliminary step, to bind a polysaccharide to a compound which already has a photoreactive crosslinking group (agent) chemically bonded thereto. Thus, upon irradiation, the photoreactive crosslinking group will facilitate crosslinking of the polysaccharide. However, prior to irradiation, such a "photoreactive polysaccharide" is capable of forming a solution so as to easily remove the unreacted crosslinking group or agent. Use of such photocrosslinkedpolysaccharides as various medical products has been attempted.

For example, U.S. Pat. Nos. 5,462,976, and 5,763,504, disclose that a photoreactive glycosaminoglycan derivative is produced by first bonding to a crosslinking agent such as cinnamic acid, thymine or coumarin into glycosaminoglycan which is a natural polymer. The resulting compound can then be purified to remove the unreacted crosslinking agent. After purification, the photoreactive polysaccharide can then be subjected to photocrosslinking using ultraviolet light to produce a photocrosslinked-glycosaminoglycan, to be used as an antiadhesive agent and a carrier for sustained-release of a drug.

Also, U.S. Pat. Nos. 6,025,444 and 6,107,410, disclose photocrosslinked products derived from photoreactive-hyaluronic acid derivatives in which, before photocrosslinking, cinnamic acid is first bound to hyaluronic acid via a spacer compound selected from: an amino acid or derivatives thereof; a peptide; amino alcohol; and, diamine.

U.S. Pat. No. 6,031,017, discloses a crosslinked hydrogel having the specific physical property which causes a preventive action for tissue adhesion. The hydrogel is produced by ultraviolet radiation of a photoreactive hyaluronic acid derivative. In the derivative, a photoreactive crosslinking group is chemically bound to a functional group of hyaluronic acid.

Other examples of photocrosslinked polysaccharides proposed for use as a medical material are: (WO02/060971 which discloses a photocrosslinked-polysaccharide sponge which can be utilized for a medical material); (U.S. Pat. No. 6,602,859, discloses a photocrosslinked hyaluronic acid proposed for use as a medical material or product). The photocrosslinked hyaluronic acid is made from a photoreactive hyaluronic acid which is proposed to have enhanced hydrophilic and filtering properties as an aqueous solution.); (JP-A-56-147802 which discloses a heparin derivative which is highly useful as an intermediate of a polymer for medical applications. The derivative is produced by reacting heparin with glycidyl acrylate or glycidyl methacrylate.); and, (U.S. Pat. No. 6,586,493 which discloses a crosslinked-product of a mixture hyaluronic acid and either glycidyl acrylate or glycidyl methacrylate bound to a non hyaluronic acid polysaccharide).

In addition to the above considerations for medical products based upon crosslinked polysaccharides, especially medical products for use as an antiadhesive agent, are the consideration that the products have a sufficient barrier effect and an appropriate degrading property. There have been repeated dilemmas caused by conventional photocrosslinked-polysaccharides used as an antiadhesive agent. In particular the product's residence in vivo becomes undesirably long if a barrier property is made high, while, if an appropriate degrading property is given, a sufficient barrier effect is not achieved. For example, when a sponge or a sheet made with a conventional photocrosslinked-polysaccharide gel having a high barrier effect is used as an antiadhesive agent, undesirable side effects can occur because the gel remains in the living body too long because of late to metabolization. Accordingly, there has been a demand for the development of medical products, particularly an antiadhesive agent, having sufficient strength and barrier effect in spite of desirable or controllable degradability in vivo.

In order to find a photocrosslinked-polysaccharide having a high barrier effect and an appropriate degrading property, the present inventor has carried out intensive studies and, as a result, has developed a photocrosslinked polysaccharide which when used as a medical product has sufficient barrier effect and an excellent early-stage degrading property. It was found that these desirable properties are provided by photocrosslinking a polysaccharide to which a specific crosslinking agent is bound.

SUMMARY OF THE INVENTION

According to one aspect of the invention, improved medical materials or products comprised of photocrosslinked polysaccharide materials such as gels, sponges, films and composites of both gel and sponge character are provided with enhanced properties. In particular the medical materials or products have improved: antiadhesion properties; strength; purity; and in vivo degradability.

According to another aspect of the invention photoreactive polysaccharides for the production of the photocrosslinked polysaccharides of the invention and medical materials comprising the photocrosslinked polysaccharide are provided.

According to another aspect of the invention, a polysaccharide is bound to a glycidyl ester which was itself formed by reaction with a photoreactive compound such as cinnamic acid, so that the resulting glycidyl ester (e.g. glycidyl cinnamate) includes a carboxyl group and an unsaturated carbon double bond. According to this aspect of the invention a photoreactive polysaccharide comprises a polysaccharide covalently bonded to a glycidyl ester represented by the formulas (1) or (2):

each represents a residue of a photoreactive compound having the carboxyl group(s) identified, and an unsaturated carbon double bond, and wherein when the polysaccharide is heparin, is neither an acryloyl group nor a methacryloyl group.

According to another aspect of the invention, the photoreactive polysaccharide is covalently bonded by an ester bond.

According to another aspect of the invention, the photoreactive polysaccharide is a monobasic carboxylic acid selected from the group consisting of cinnamic acid, hydroxycinnamic acid, acrylic acid, methacrylic acid, furylacrylic acid, thiopheneacrylic acid, cinnamylideneacetic acid and sorbic acid, or dibasic carboxylic acid selected from the group consisting of maleic acid and fumaric acid.

According to a preferred embodiment of the invention, the photoreactive compound of the photoreactive polysaccharide is cinnamic acid.

According to another aspect of the invention, the polysaccharide is selected from the group consisting of glycosaminoglycan, poly(uronic acid), poly(amino sugar), glucan, mannan, fructan, galactan, pectin substance, plant gum, agar, porphyran, carrageenan, fucoidan and a pharmaceutically acceptable salt or derivative thereof.

According to another embodiment of the invention, the polysaccharide is a glycosaminoglycan selected from the group consisting of hyaluronic acid, chondroitin, chondroitin sulfate, dermatan sulfate, heparin, heparan sulfate and keratan sulfate. The poly(uronic acid) is alginic acid; the glucan derivative is carboxymethyl cellulose; and the poly(amino sugar) or derivative thereof is selected from the group consisting of chitin and chitosan.

In another preferred embodiment, the polysaccharide is hyaluronic acid and the photoreactive compound is cinnamic acid.

According to another aspect of the invention, the photoreactive compound is a carboxylic acid selected from the group consisting of cinnamic acid, hydroxycinnamic acid, maleic acid, fumaric acid, acrylic acid, methacrylic acid, furylacrylic acid, thiopheneacrylic acid, cinnamylideneacetic acid and sorbic acid; and, the polysaccharide is selected from the group consisting of hyaluronic acid, chondroitin, chondroitin sulfate, dermatan sulfate, heparan sulfate, keratan sulfate, chitin, chitosan, alginic acid and carboxymethyl cellulose.

In one embodiment of the invention, the photoreactive compound is a carboxylic acid selected from the group consisting of cinnamic acid, hydroxycinnamic acid, maleic acid, fumaric acid, furylacrylic acid, thiopheneacrylic acid, cinnamylideneacetic acid and sorbic acid; and, the polysaccharide is a polysaccharide selected from the group consisting of heparin, chitin, chitosan, alginic acid and carboxymethyl cellulose.

According to yet another aspect of the invention a photocrosslinked-polysaccharide is produced by crosslinking the photoreactive polysaccharides summarized above.

According to one aspect of the invention, a photocrosslinked-polysaccharide in the state of a gel is produced by irradiating with light a solution of the photoreactive polysaccharides described above.

According to another aspect of the invention, a photocrosslinked-polysaccharide in the state of sponge is produced by freezing or freeze-drying a solution of the photoreactive polysaccharides summarized above, and irradiating the resulting frozen solution or freeze-dried product with light.

According to another aspect of the invention, a photocrosslinked-polysaccharide having both properties of a gel-state product and a sponge-state product is produced by:

(a) irradiating a solution of the photoreactive polysaccharide with light to obtain a gel-state product;
freezing the gel-state product; and,
irradiating the frozen gel-state product with light while keeping the frozen state; or by, (b) irradiating a solution of the photoreactive polysaccharide with light to obtain a gel-state product;
freeze-drying the gel-state product; and,
irradiating the freeze-dried gel state product with light.

According to another aspect of the invention, a photocrosslinked-polysaccharide in the state of a film is produced by drying a solution of the photoreactive polysaccharide described above to obtain a film thereof, and irradiating the film with light.

According to another aspect of the invention, a photocrosslinked-polysaccharide is produced by the steps comprising:

irradiating a solution of a photoreactive polysaccharide as described above, with light to obtain a gel-state product;
freezing the gel-state product;
irradiating the frozen gel-state product with light while keeping the frozen state to obtain a composition with both properties of gel-state product and sponge-state product; and, drying the composition, and
irradiating the composition thus dried with light.

According to another aspect of the invention, medical materials and products employing the photocrosslinked-polysaccharides are made, including an antiadhesive agent; a substrate for sustained drug release; and a substrate for culturing cells.

DETAILED DESCRIPTION

Hereinafter, the present invention is described below in detail by way of detailed embodiments and methods. These detailed descriptions are intended only to be examples of the inventions disclosed and claimed herein and are in no way intended to limit the scope of the invention which is particularly pointed out and distinctly claimed in the numbered claims appended hereto.

Photoreactive Polysaccharide Composition

In a photoreactive polysaccharide of the present invention, a glycidyl ester represented by the above-described formulas (1) and (2) is bound to a polysaccharide via a covalent bond. The polysaccharide constituting the "photoreactive polysaccharide" includes glycosaminoglycan, poly(uronic acid), poly(amino sugar), glucan, mannan, fructan, galactan, pectin substance, plant gum, agar, porphyran, carrageenan, fucoidan and a pharmaceutically acceptable salt or derivative thereof. Among these, glycosaminoglycan or a salt or derivative thereof is particularly preferred in the present invention.

Glycosaminoglycan (hereinafter sometimes referred to as "GAG") is a polysaccharide having a basic skeleton containing an amino sugar and uronic acid (or galactose). Examples of GAG include hyaluronic acid, chondroitin, chondroitin sulfate, dermatan sulfate, keratan sulfate, heparin and heparan sulfate. Hyaluronic acid, chondroitin sulfate, heparin, heparan sulfate and keratan sulfate are preferred, and hyaluronic acid is more preferred. Examples of pharmaceutically acceptable salts include alkali metal salts such as sodium and potassium salts; alkali earth metal salts such as a calcium salts; salts with an inorganic base such as ammonium salts; and, salts with an organic base such as pyridine salts, diethanolamine salts, cyclohexylamine salts and amino acid salts. Sodium salts are particularly preferred.

The derivatives of glycosaminoglycan include sulfated derivatives in which one or more than one sulfuric acid groups are bound to GAG on purpose, desulfated derivatives in which sulfuric acid groups are partially or completely removed from GAG, oxidized/reduced derivatives in which GAG is subjected to oxidation/reduction reaction, and oxidized/reduced-desulfated derivatives in which oxidized/reduced derivatives of GAG are desulfated.

Examples of sulfated derivatives include sulfated hyaluronic acid and chondroitin polysulfuric acid.

Examples of the desulfated derivative include: a 6-desulfated heparin in which the sulfate groups at the 6-position hydroxyl groups of glucosamine residues constituting heparin are removed (cf. U.S. Pat. No. 6,492,503); a 2-desulfated heparin in which the sulfate groups at the 2-position hydroxyl groups of hexuronic acid residues or the sulfate groups at the 2-position amino groups of glucosamine residues constituting heparin are removed (cf. JP-A-2003-113090); and, completely desulfated heparin.

Examples of oxidized/reduced-desulfated derivative are periodic acid oxidized/reduced-desulfated heparin in which the bondage between the 2- and 3-position carbon atoms of hexuronic acid is partially cleaved and a part of the uncleaved hexuronic acid has no sulfate group on its 2-position (cf. U.S. Pat. No. 6,498,246 and the like). Among the above examples, desulfated derivatives and oxidized/reduced-desulfated derivatives are preferred and desulfated derivatives are particularly preferred.

On the other hand, polysaccharides other than glycosaminoglycan (which may be mentioned as other polysaccharides) include poly(uronic acid), poly(amino sugar), glucan, mannan, fructan, galactan, pectin substance, plant gum, agar, porphyran, carrageenan, fucoidan and a salt or derivatives thereof. The poly(uronic acid) includes alginic acid. The poly(amino sugar) and deacetylated derivatives thereof include chitin and chitosan. Examples of glucan and derivatives thereof include amylose, amylopectin, glycogen, cellulose, hydroxymethyl cellulose and carboxymethyl cellulose. The salt of other polysaccharides include those which are listed hereinabove as the glycosaminoglycan salts. The derivatives of other polysaccharides include the above-described carboxymethyl derivatives, hydroxymethyl derivatives and deacetylated derivatives. In the above-described other polysaccharides and derivatives thereof, chitin, chitosan, alginic acid and carboxymethyl cellulose are particularly preferred.

The molecular weight (weight-average molecular weight) of the above-described polysaccharides used for the photoreactive polysaccharides of the present invention is as follows. In the case of polysaccharides other than hyaluronic acid, the molecular weight is usually 2,000 to 3,000,000, preferably 3,000 to 2,700,000, and more preferably 4,000 to 2,500,000. In the case of hyaluronic acid, the molecular weight is usually 20,000 to 3,000,000, preferably 100,000 to 2,000,000, and more preferably 200,000 to 1,200,000.

The polysaccharides of the present invention may be derived from natural products, may be chemically synthesized or may be produced in microorganisms such as yeast by genetic engineering. Generally, GAG can be produced by extracting from partial materials of living organisms (such as cockscomb, umbilical cord, cartilage, skin, small intestine, blood vessel, etc.), and preferred examples are the same.

In the present invention, the photoreactive compounds having a carboxyl group and an unsaturated carbon-carbon double bond in a molecule which forms of the glycidyl ester represented by the above-described formulas (1) and (2), are acrylic acid, derivatives thereof, and methacrylic acid represented by the following formula (3):

wherein $R^3$ represents hydrogen, phenyl, hydroxyphenyl, carboxyl, furyl, thienyl, styryl or 1-propenyl, and $R^4$ represents hydrogen or methyl, and wherein when $R^4$ is methyl, $R^3$ is hydrogen.

Examples of the photoreactive compound include monobasic carboxylic acids such as cinnamic acid, hydroxycinnamic acid, acrylic acid, methacrylic acid, furylacrylic acid, thiopheneacrylic acid, cinnamylideneacetic acid and sorbic acid, and dibasic carboxylic acids such as maleic acid and fumaric acid. Among these, preferred ones are carboxylic acids having one unsaturated group such as cinnamic acid or thiopheneacrylic acid and carboxylic acid having two unsaturated groups such as cinnamylideneacetic acid or sorbic acid. In view of safety to the living body, cinnamic acid is most preferred.

The glycidyl ester of the photoreactive compound having a carboxyl group and an unsaturated carbon double bond is produced by reacting the above-described photoreactive compound with epihalohydrin, preferably epichlorohydrin. When the photoreactive compound is a dibasic carboxylic acid such as maleic acid or fumaric acid, a mono-ester or a di-ester is produced as a glycidyl ester, and a di-ester is preferred.

The photoreactive polysaccharide of the present invention is produced by introducing the above-described photoreactive glycidyl ester into the above-described polysaccharide. An epoxy group of the glycidyl ester is opened and is bound via a covalent bond to a carboxyl group, a hydroxyl group or an amino group of the polysaccharide. The photoreactive polysaccharide is preferably one in which a glycidyl ester of the photoreactive compound is bound via an ester bond to a carboxyl group of the carboxyl group-containing polysaccharide such as hyaluronic acid, chondroitin, chondroitin sulfate, dermatan sulfate, heparan sulfate, heparin, alginic acid, carboxymethyl cellulose.

The preferred photoreactive polysaccharide of the present invention is one in which the photoreactive compound of the above-described glycidyl ester is a carboxylic acid selected from the group consisting of cinnamic acid, hydroxycinnamic acid, maleic acid, fumaric acid, acrylic acid, methacrylic acid, furylacrylic acid, thiopheneacrylic acid, ciannamylideneacetic acid and sorbic acid, and the polysaccharide is a polysaccharide selected from the group consisting of hyaluronic acid, chondroitin, chondroitin sulfate, dermatan sulfate, heparan sulfate, keratan sulfate, chitin, chitosan, alginic acid and carboxymethyl cellulose.

Other preferred photoreactive polysaccharides have a photoreactive polysaccharide in which the photoreactive compound of the above-described glycidyl ester is a carboxylic acid selected from the group consisting of cinnamic acid, hydroxycinnamic acid, maleic acid, fumaric acid, furylacrylic acid, thiopheneacrylic acid, cinnamylideneacetic acid and sorbic acid, and the polysaccharide is a polysaccharide selected from the group consisting of heparin, chitin, chitosan, alginic acid and carboxymethyl cellulose.

Among the above-described photoreactive polysaccharides, the most preferred one is a photoreactive polysaccharide in which the photoreactive compound of the above-described glycidyl ester is cinnamic acid and the polysaccharide is hyaluronic acid.

Photoreative Polysaccharide Synthesis

The photoreactive polysaccharides of the present invention can be produced by the following methods.

A reverse precipitation method may be employed as follows.

An organic solvent which is miscible with water and will not react with a photoreactive glycidyl ester is added to a 0.1 to 15 wt % aqueous solution of a polysaccharide having a carboxyl group to give a mixing ratio with water in the aqueous solution of 0 to 50%. A photoreactive glycidyl ester is added thereto so as to give a concentration of 0.1 to 10 wt %, followed by stirring at 40 to 80° C. for 0.5 to 240 hours. Next, sodium chloride in an amount of 0.5- to 5-fold of the weight of the polysaccharide used is added thereto. The mixture is poured into ethanol in an amount of 2- to 5-fold of the amount of the reaction solution and the precipitate is separated. The precipitate is filtered using a filter, well washed with ethanol and dried to give a photoreactive polysaccharide.

A normal precipitation method may also be employed as follows An organic solvent which is miscible with water and which will not react with a photoreactive glycidyl ester, is added to a 0.1 to 15 wt % aqueous solution of a polysaccharide having a carboxyl group to give a mixing ratio with water in the aqueous solution of 0 to 50%. A photoreactive glycidyl ester is added thereto to give a concentration of 0.1 to 10 wt %, followed by stirring at 40 to 80° C. for 0.5 to 240 hours. Next, sodium chloride in an amount of 0.5- to 5-fold of the weight of the polysaccharide used is added thereto. Then ethanol in an amount of 0.5- to 5-fold of the amount of the reaction solution is poured thereinto and the precipitate is separated. The precipitate is filtered using a filter, well washed with ethanol and dried to give a photoreactive polysaccharide.

An amount of the above-described glycidyl esters which are to be introduced into a polysaccharide to provide a photoreactive polysaccharide according to the present invention or, in other words, the degree of substitution of a photoreactive group (unsaturated carbon double bond), is decided in consideration of the desired crosslinking ratio of the photocrosslinked-polysaccharide. However, the degree of substitution varies depending on the kind of polysaccharide and of the photoreactive compound constituting the photoreactive glycidyl ester. For example, the degree of substitution is selected by considering the molecular weight of the polysaccharide and the types and numbers of the reactive group such as a carboxyl group, a hydroxyl group or an amino group in the polysaccharide and an unsaturated group of the photoreactive compound. As described in "Examples" below, the amount or degree of substitution of the photoreactive group in the photoreactive polysaccharide is represented by a percentage of the number of the photoreactive groups which are introduced into a constituting unit of the polysaccharide such as a repeating disaccharide unit constituting glycosaminoglycan. Although the degree of substitution of the photoreactive group depends upon the kind of polysaccharide, it is usually about 1 to 20%, preferably about 1 to 15%.

Crosslinking The Polysaccharides

Photocrosslinked-polysaccharides of the present invention are a product crosslinked by light irradiation of the above-described photoreactive polysaccharides. A cyclobutane-type ring is formed by the photoreactive groups bonding to each other. In particular, the carbon-carbon double bonds from respective photoreactive polysaccharide molecules, bond to each other. This bonding provides a network structure.

It is preferred that light irradiation of the photoreactive polysaccharide is carried out under such conditions that the photoreactive group efficiently causes a photodimerization reaction. Although the light to be used for the light irradiation is not particularly limited, ultraviolet light is preferred when the photoreactive compound is cinnamic acid. A wavelength of ultraviolet light should be chosen so as not to cleave a glycoside bond of the photoreactive polysaccharide, but should cause a photodimerization reaction of the photoreactive group. A wavelength of 200 to 600 nm for example may be used according to this criteria. With regard to an ultraviolet lamp, a high pressure mercury lamp or a metal halide lamp is preferred. Preferably, if necessary, undesired wavelengths may be removed from the light source, for example, by a cut filter. A preferred dose of the irradiated light is about 0.01 to 200 J/cm$^2$ and is appropriately selected depending on the desired form (gel, sponge, composite or film).

The crosslinking ratio of the photocrosslinked-polysaccharide of the present invention varies depending on the degree of substitution of the photoreactive group introduced into the above-described photoreactive polysaccharide, conditions of the closslinking reaction, and the like, but it is usually about 1 to 60%. The crosslinking ratio can be determined by a measuring method given in the Examples described below.

In the present invention, when conditions in the step of light irradiation of the photoreactive polysaccharide are changed, various forms of product such as gel, sponge, composite, composite film or film can be provided.

Crosslinked Gel

According to one aspect of the invention, the polysaccharide can be crosslinked to a degree to form a three dimensional structure which holds water to form a "hydrogel." The photocrosslinked-polysaccharide gel can be produced by a known method mentioned, as disclosed for example, in U.S. Pat. No. 6,031,017. When the polysaccharide is hyaluronic acid, for example, there may be used a method including steps in which a solution of a photoreactive hyaluronic acid according to the invention is first prepared. The solution is made into a form or shape in which ultraviolet light is apt to permeate, and ultraviolet light is irradiated into the solution. More details of the producing method may be referred to as method mentioned in U.S. Pat. No. 6,031,017. An aqueous medium for the photoreactive hyaluronic acid solution upon exposure to ultraviolet irradiation includes water, buffer, physiological saline, buffered physiological saline, and the like. When the product is to be used for a medical material, buffer, physiological saline and buffered physiological saline are preferably used.

Crosslinked Sponge

According to the present invention, the photocrosslinked-polysaccharide employed in a spongy form is a porous substance having independent foams or connecting foams, has elasticity, shows excellent water absorbing property and water discharging property and is insoluble in water and other aqueous media. More specifically, it is a substance having such a property that, when the spongy photocrosslinked-polysaccharide in a dry state is dipped in water or in other aqueous medium, it quickly absorbs water and swells and, when it is pressurized after swelling or placed on a water-absorbing paper, liquid medium such as water absorbed therewith is quickly discharged. Although the porous structure of sponge is different depending on the kinds, manufacturing conditions, and the like of the photoreactive polysaccharide, 50% or more of all of the pores per unit area usually have a pore size of 10 to 50 μm whereby absorption and release of a liquid medium are excellent and strength is also well maintained.

A method for the manufacture of a photocrosslinked-polysaccharide-sponge contains the steps of (A) freezing or freeze-drying a solution of a photoreactive polysaccharide made in accordance with the invention, and (B) irradiating the frozen solution or the freeze-dried product with light to give a photocrosslinked-polysaccharide sponge in which the photoreactive polysaccharide is crosslinked. More specifically, a sponge can be manufactured by the method disclosed in WO 02/060971, and the pore size can also be measured by the method disclosed in WO 02/060971, both of which references are incorporated herein.

Crosslinked Composite Gel/Sponge

According to the present invention, a photocrosslinked-polysaccharide having both properties of gel and sponge (hereinafter referred to a photocrosslinked-polysaccharide composite) can be produced by combination of the above-described method for preparation of the photocrosslinked-polysaccharide gel with the above-described method for preparation of the photocrosslinked-polysaccharide sponge and is a product having the characteristics of both gel and sponge materials. More specifically, the composite has both a high barrier effect which is exhibited by a photocrosslinked-polysaccharide gel and a high strength which is exhibited by a photocrosslinked-polysaccharide sponge.

A method for producing the photocrosslinked-polysaccharide composite of the present invention by way of example when the polysaccharide is hyaluronic acid, is as follows. An aqueous solution of photoreactive hyaluronic acid at high concentration is prepared. The solution is formed into such a shape that ultraviolet light is apt to permeate the form, and irradiation is provided to give a gel-state product. The resulting gel-state product is frozen and the frozen product is further irradiated with ultraviolet light while keeping the frozen-state or, after the gel-state product is freeze-dried, the freeze-dried product is further irradiated with ultraviolet light. Both of these methods provide the composite form of the crosslinked polysaccharide.

Composite Film

According to the present invention, the phocrosslinked-polysaccharide composite of the present invention can be employed as a film by the following methods. The above-described photocrosslinked-polysaccharide composite is dried to be a thin film and subsequently the thin film is irradiated with ultraviolet light to get a product in a film (hereinafter referred to as photocrosslinked-polysaccharide composite film). The photocrosslinked-polysaccharide composite film shows much better effect as a barrier to a wound and higher strength than the photocrosslinked-polysaccharide composite.

Crosslinked Film

The photocrosslinked-polysaccharide film of the present invention can be produced in such a manner that a solution of a photoreactive polysaccharide according to the invention is applied for example on a substrate, in a desired thickness. Then a thin film is produced by drying it with air and the resulting thin film is irradiated with ultraviolet light. More specifically, it can be produced by a method disclosed in U.S. Pat. Nos. 5,462,976 and 5,763,504. The photocrosslinked-polysaccharide film of this present invention has an extreme barrier property, however once it gets wet it becomes slippery and weak for strength.

In the conventional method wherein a polysaccharide is crosslinked using diglycidyl ether as a crosslinking agent (such as a method mentioned in *Eur. J. Pharm. Sci.*, 2002 March; 15(2):139-48), crosslinking is directly formed between polysaccharides whereby the polysaccharide's physical and chemical properties are modified. On the other hand, the above-described method for the manufacture of a photocrosslinked-polysaccharide product such as gel, sponge, composite or film according to the present invention is greatly different therefrom in view of the following respects and provides great enhancement over prior compounds.

First, in the method of the present invention, a desired form of a product is formed at the photocrosslinking step because the polysaccharide itself is photoreactive due to its previous bonding with a photoreactive compound. According to the invention, no crosslinking takes place at all in the stage for producing the photoreactive polysaccharide in which a glycidyl ester of the photoreactive compound is introduced into a polysaccharide and, therefore, the unreacted glycidyl ester of the photoreactive compound is not caged in the photoreactive polysaccharide but can be removed by sufficient washing and purification.

It is also possible according to the present invention for a reaction solution of the polysaccharide with the glycidyl ester of the photoreactive compound to be poured into ethanol and whereupon precipitate is separated whereby a pure photoreactive polysaccharide is produced. The reason is that the glycidyl ester of the photoreactive compound is hardly soluble in water and easily soluble in ethanol while the photoreactive polysaccharide which is a reaction product is hardly soluble in ethanol. Thus, most of unreacted glycidyl ester of photoreactive compound is dissolved in ethanol and is not incorporated into the precipitate. When the resulting precipitate of the photoreactive polysaccharide is further and well washed with ethanol, the unreacted glycidyl ester of the photoreactive compound adhered therearound can be easily washed out and, therefore, the photoreactive polysaccharide can be produced in a very high purity.

When glycidyl ester of the photoreactive compound is introduced into a polysaccharide, no other condensing agent and catalyst are necessary and, therefore, contamination with unnecessary substances can be avoided. Moreover, since a crosslinked product can be produced by light irradiation after making the photoreactive polysaccharide into a desired shape, it is now possible to give a crosslinked product in a shape meeting the use.

Medical Materials/Products

The photocrosslinked-polysaccharide of the present invention can be used as "medical materials" or "medical products" such as a medical product for prevention of adhesion among the tissues after operation ("antiadhesive agent"), a medical product for constitution of a device for sustained drug release ("substrate for sustained drug release"), a substrate for scaffold in cell culturing ("substrate for culturing cells"), a medical product for protection of a wound ("wound coating material"), a medical product for maintaining the space in living body ("space maintaining material"), a medical product for filling the hollow of connective tissue such as bone ("bone filler"), an artificial body fluid (artificial synovial fluid, artificial lacrimal fluid, supplementary product for ophthalmologic operation, etc.), a product for moisturization of surface of living body ("moisturizer"), an additive which is added for maintaining the dosage form of pharmaceuticals, etc. ("excipient"), and the like. It is particularly useful as an antiadhesive agent, a substrate for sustained drug release or a substrate for culturing cells. In addition, products according to the invention in the form of a sponge, a composite, and a film, are particularly useful as antiadhesive agents because of the photocrosslinked polysaccharide's excellent degradability in spite of its strength.

The photocrosslinked-polysaccharide of the present invention can be used as a substrate for sustained release of a drug which is embedded in the three-dimensional network structure of the photocrosslinked-polysaccharide. There is no particular limitation for the drug, so long as it can be control-released by being held in the network structure of the photocrosslinked-polysaccharide of the present invention, however, the following drugs are examples.

Nonsteroidal anti-inflammatory and analgesic agents such as salicylic acid, aspirin, mefenamic acid, tolfenamic acid, flufenamic acid, diclofenac, sulindac, fenbufen, indomethacin, acemetacin, amfenac, etodolac, felbinac, ibuprofen, flurbiprofen, ketoprofen, naproxen, pranoprofen, fenoprofen, tiaprofen acid, oxaprozin, loxoprofen, aluminoprofen, zaltoprofen, piroxicam, tenoxicam, lornoxicam, meloxicam, tiaramide, tolmetin, diflunisal, acetaminophen, floctafenine, tinoridine, tiaramide hydrochloride and mepirizole.

Anticancer agents such as methotrexate, fluorouracil, vincristine sulfate, mitomycin C, actinomycin C and daunorubicin hydrochloride.

Antiulcer agents such as aceglutamide aluminum, L-glutamine, p-(trans-4-aminomethylcyclohexanecarbonyl)phenylpropionic acid hydrochloride, cetraxate hydrochloride, sulpiride, gefarnate and cimetidine.

Enzyme preparations such as chymotrypsin, streptokinase, lysozyme chloride, bromelain and urokinase.

Antihypertensive agents such as clonidine hydrochloride, bunitrolol hydrochloride, bunazosin hydrochloride, captopril, bethanidine sulfate, metoprolol tartrate and methyidopa.

Agents for diuretic organs such as flavoxate hydrochloride.

Anticoagulants for blood such as heparin, dicumarol and warfarin.

Agents for arteriosclerosis such as clofibrate, simfibrate, elastase and nicomol.

Agents for circulatory organs such as nicardipine hydrochloride, nimodipine hydrochloride, cytochrome C and tocopherol nicotinate.

Steroidal agents such as hydrocortisone, prednisolone, dexamethasone and betamethasone.

Promoters for healing the wound such as growth factor and collagen (refer to JP-A-60-222425).

Other examples include physiologically active polypeptides, hormone, antituberculous agents, hemostatic agents, remedies for diabetes, vasodilators, remedy for arrhythmia, cardiotonic agents, antiallergic agents, antidepressants, antiepileptic agents, muscle relaxants, antitussive/expectorants, antibiotics and the like.

The photocrosslinked-polysaccharides of the present invention are also useful as a substrate for culturing cells or tissues when a medium for culturing cells (including cultured cells and primary cultured cells) and tissue (such as tissue pieces taken out from the living body) are impregnated into the photocrosslinked-polysaccharide so that the medium is well contained therein.

There is no particular limitation for "cells" and "tissues" which are applied to the culturing substrate of the present invention, so long as they are cells and tissues which can be grown outside the living body. Specific examples thereof include cells/tissue derived from mesoderm, preferred examples include cells/tissues derived from connecting tissue, and particularly preferred examples include epidermal cells, cartilage cells, hepatic cells and neuroblast.

DETAILED EXAMPLES

Hereinafter, aspects of the present invention are illustrated in more detailed Examples. In the following Examples a percent concentration means a weight percent concentration unless otherwise stated.

Analytical methods and the like used in the Examples are illustrated as follows.

Measurements of epoxy equivalent were carried out according to an epoxy equivalent test method for epoxy resins disclosed in JIS K7236:2001 incorporated herein be reference.

Measurement of rotational viscosity were carried out using a rotational viscometer of type E (TOKI RE-8OH; manufactured by Toki Sangyo). When a product having a rotational viscosity of more than 50 Pa.s was tested, measurement was carried out at 25° C. and 1.0 rpm using 3° cone of 14 mm diameter. On the other hand, when a product having rotational viscosity of 50 Pa.s or less was tested, measurement was carried out at 20° C. and 1.0 rpm using 1° cone of 24 mm diameter. However, when a product having a rotational viscosity of around 50 Pa.s is tested, measurement under any of the conditions may be done.

Measurement of breaking tenacity was carried out using a Texture Analyzer TA-XT2 (manufactured by Stable Micro Systems). Product tested was previously well swollen in distilled water and was cut out a rectangle in a size of 6×2.5 cm to get a product to be tested. The product was set on a stage of the analyzer and it was pushed with a spherical probe of 12.7 mm diameter at a speed of 1 mm/sec. Breaking tenacity was determined at the point when the probe pierced the product.

Measurement of degree of substitution of photoreactive crosslinking group means the value in terms of percent of the numbers of the photoreactive crosslinking group introduced into a repeating disaccharide unit of glycosaminoglycan. An amount of glycosaminoglycan necessary for calculation of the degree of substitution was measured by a method for the measurement of carbazole utilizing a calibration curve while an amount of the photoreactive crosslinking group was measured by a method for the measurement of absorbance utilizing a calibration curve.

Measurement of crosslinking ratio was determined as follows. First, a product to be tested (1 g) was saponified for 1 hour with 1 ml of 1 mol/l aqueous solution of sodium hydroxide, the resulting solution was made acidic, and substances derived from photoreactive crosslinking group (monomer and dimer) were extracted with ethyl acetate. The extract was analyzed by high-performance liquid chromatography (HPLC) and an amount of the dimer was measured by a calibration method. Then, molar numbers of the photoreactive crosslinking group converted into the dimer of the photoreactive crosslinking group introduced into glycosaminoglycan were expressed in percent and used as a crosslinking ratio.

Reference Example 1

(Synthesis of Glycidyl Ester of Photoreactive Compound.)
1. Synthesis of Glycidyl Cinnamate.

To 7.5 g of trans-cinnamic acid (manufactured by Wako Pure Chemical) were added 3 g of tetraethylammonium bromide (manufactured by Wako Pure Chemical) and 100 ml of epichlorohydrin (manufactured by Wako Pure Chemical), the mixture was heated to reflux at 110° C. for 3 hours, 50 ml of distilled water was added thereto, an organic layer was separated, concentrated in vacuo at 80° C. and distilled under reduced pressure of 6 mmHg and the fraction of 130 to 160° C. was recovered to give 12 g of glycidyl cinnamate. An epoxy equivalent of this glycidyl cinnamate was 240.3.

The resulting glycidyl cinnamate was analyzed by gas chromatography. In the gas chromatography, GC-17A (manufactured by Shimadzu) was used and the measurement was carried out using a column DB-5 (membrane thickness: 0.5 μm; inner diameter: 0.25 mm; length: 30 m) at the column temperature of 100° C. (0 to 5 minutes) to 250° C. (increasing at 5° C./minute) (cf. FIG. 1). As a result, the maximum peak was found at 32.6 min and production of glycidyl cinnamate could be confirmed.

Figure 1:
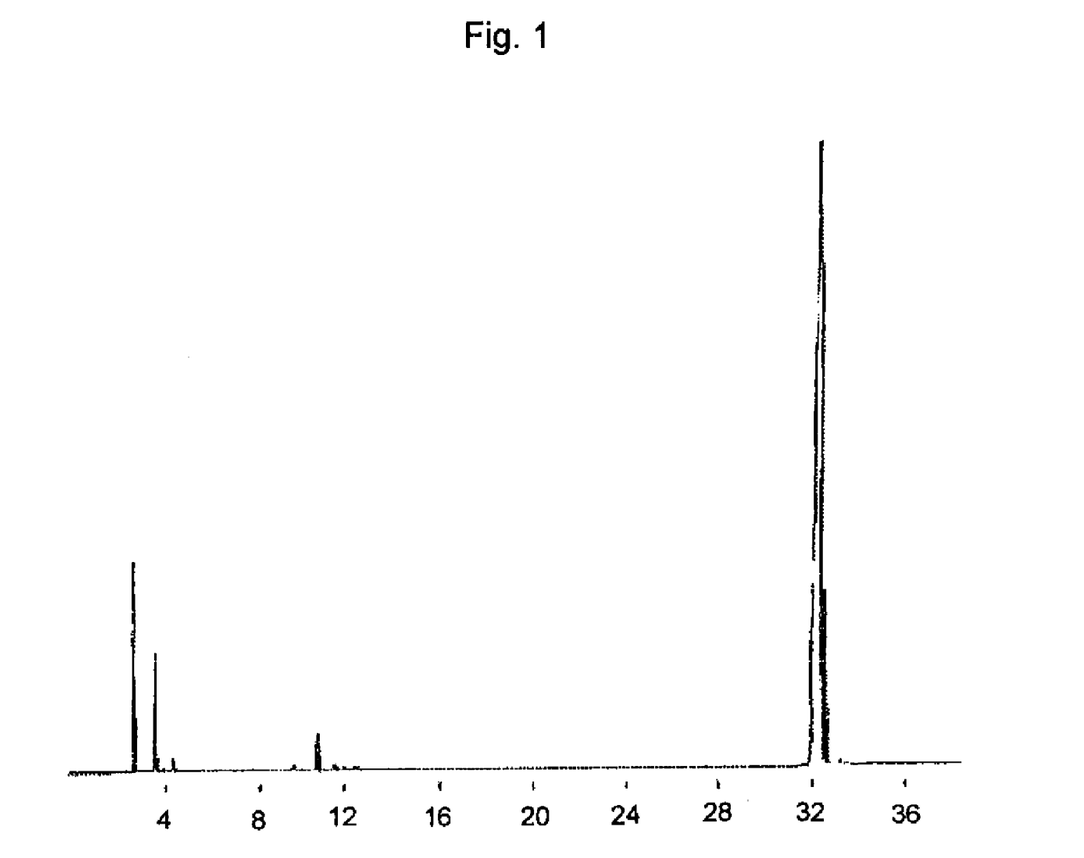
FIG. 1 shows a result of measurement of glycidyl cinnamate in Reference Example 1 by gas chromatography. In the drawing, the abscissa means time (in minute(s)).

| Peaks | Epichlorohydrin | 3.6 min |
|---|---|---|
| | trans-Cinnamic acid | 22.5 min |
| | Glycidyl cinnamate | 32.6 min |

2. Synthesis of Glycidyl Thiopheneacrylate.

To 2.5 g of trans-3-3-thiopheneacrylic acid (manufactured by Aldrich) were added 1 g of tetraethylammonium bromide (manufactured by Wako Pure Chemical) and 60 ml of epichlorohydrin (manufactured by Wako Pure Chemical), the mixture was heated to reflux at 110° C. for 3 hours, 30 ml of distilled water was added thereto and an organic layer was separated and concentrated in vacuo at 80° C. to give 6.5 g of glycidyl thiopheneacrylate. An epoxy equivalent of this glycidyl thiopheneacrylate was 596.8.

3. Synthesis of Glycidyl Cinnamylideneacetate.

To 9.0 g of cinnamylideneacetic acid (manufactured by Lancaster) were added 3.5 g of tetraethylammonium bromide (manufactured by Wako Pure Chemical) and 100 ml of epichlorohydrin (manufactured by Wako Pure Chemical), the mixture was heated to reflux at 110° C. for 3 hours, 50 ml of distilled water was added thereto and an organic layer was separated and concentrated in vacuo at 80° C. to give 17.3 g of glycidyl cinnamylideneacetate. An epoxy equivalent of this glycidyl cinnamylideneacetate was 444.3.

4. Synthesis of Glycidyl Sorbate.

To 1.8 g of sorbic acid (manufactured by Wako Pure Chemical) were added 1 g of tetraethylammonium bromide (manufactured by Wako Pure Chemical) and 60 ml of epichlorohydrin (manufactured by Wako Pure Chemical), the mixture was heated to reflux at 110° C. for 3 hours, 30 ml of distilled water was added thereto and an organic layer was separated and concentrated in vacuoat 80° C. to give 3.5 g of glycidyl sorbate. An epoxy equivalent of this glycidyl sorbate was 367.4.

Example 1

(Manufacture of Hyaluronic Acid into which Glycidyl Cinnamate is Introduced (Hereinafter Sometimes Referred to as GLCN-HA) and a Crosslinked Product Thereof).
1-(1). Synthesis of GLCN-HA (Reverse Precipitation Method)

To 100 ml of a 1 wt % aqueous solution of hyaluronic acid (weight-average molecular weight: 800,000) were added 50 ml of water for injection and 75 ml of 1,4-dioxane, and 3 ml of glycidyl cinnamate (epoxy equivalent: 240.3) was added thereto, followed by stirring for 24 hours in a constant-temperature vessel of 50° C.

Sodium Chloride (1 g) was added to the above described solution, followed by stirring, and the mixture was poured into 800 ml of ethanol to give a cotton-like precipitate. The precipitate was well washed with ethanol and dried to give 1.1 g of GLCN-HA. The degree of substitution of glycidyl cinnamate was 2.9%.

1-(2). Synthesis of GLCN-HA (Normal Precipitation Method).

Sodium Chloride (1 g) was added to the solution prepared in the same manner as in 1-(1) followed by stirring and 500 ml of ethanol was slowly poured thereon to give a powdery precipitate. The precipitate was well washed with ethanol and dried to give 1.1 g of GLCN-HA. The degree of substitution of glycidyl cinnamate was 3.5%.

1-(3). Synthesis of GLCN-HA (Normal Precipitation Method).

Sodium Chloride (1 g) was added to the solution prepared by the same reaction as in 1-(1), except that stirring was carried out for 48 hours in a constant-temperature vessel of 60° C., followed by stirring, and about 500 ml of ethanol was slowly poured thereon to give a powdery precipitate. The precipitate was well washed with ethanol and dried to give 1.1 g of GLCN-HA. The degree of substitution of glycidyl cinnamate was 10.1%.

Preparation of Photocrosslinked-Hyaluronic Acid Gel.

GLCN-HA produced in 1-(1) was dissolved in distilled water to give a concentration of 3% and the resulting aqueous solution was placed in a hard glass container having 1 mm space and irradiated with ultraviolet ray thereto using a 3-kW metal halide lamp (manufactured by Ushio Denki) at a dose of 25.0J/cm$^2$ (measuring wavelength: 280 nm) on one side whereby 50.0J/cm$^2$ in total for both sides to produce a gel-state product. The measured crosslinking ratio and isomerization ratio of the resulting gel-state product were 18.4% and 71.4%, respectively.

The measured rotational viscosity of 0.5 ml of the gel-state product was 142.0 Pa.s. The rotational viscosity of an aqueous solution of GLCN-HA without ultraviolet ray irradiation was 83.0 Pa.s.

An isomerization ratio is a ratio of conversion of trans-cinnamic acid to cis-cinnamic acid. Since cis-cinnamic acid is produced after an excited state which is necessary for trans-cinnamic acid in the formation of a double bond, it is an index for judging whether the photoreaction was appropriately carried out and the value is quantitatively calculated by previously preparing a calibration curve of cis-cinnamic acid.

Preparation Of Photocrosslinked-Hyaluronic Acid Film.

GLCN-HA produced in 1-(1) was dissolved in distilled water to give a concentration of 1%, 5 ml of the resulting aqueous solution was poured into a plastic Petri dish having a diameter of 50 mm and dried by placing in a constant-temperature vessel of 50° C. to prepare a transparent film. Both sides of the film were irradiated with ultraviolet ray from an 800-W high-pressure mercury lamp (manufactured by Orc Seisakusho) at a dose of each 2.5 J/cm$^2$ per side (measuring wavelength: 280 nm) to give a water-insoluble product in a film. The measured crosslinking ratio and isomerization ratio of this filmy product were 7.2% and 68.5%, respectively.

When the product in a film produced by ultraviolet ray irradiation was dipped in water, it was immediately swollen and, even when it was just allowed to keep in water at room temperature for one month, the shape was still maintained. The measured breaking tenacity of the product after swelling was 29.8 g.

Preparation Of Photocrosslinked-Hyaluronic Acid Sponge (1).

GLCN-HA produced in 1-(1) was dissolved in distilled water to give a concentration of 3%, the resulting aqueous solution was filled in a high-density polyethylene bag, sealed, sandwiched between two hard glass plates having a gap of 1 mm and frozen in an ethanol bath of −40° C. While keeping the frozen state, ultraviolet ray of 2.0 J/cm$^2$ (measuring wavelength: 280 nm) per one side was irradiated using an 800-W high-pressure mercury lamp (manufactured by Orc Seisakusho), followed by melting to give a product in a sponge (hereinafter referred to as GLCN-HA Sponge (1)). The measured crosslinking ratio and isomerization ratio of this spongy product were 16.8% and 68.2%, respectively.

In the product which was melted once again without irradiating with ultraviolet ray after freezing, it was still in a state of solution and no change in physical property was found at all. The measured breaking tenacity of the resulting spongy product was measured 178.7 g.

Preparation of Photocrosslinked-Hyaluronic Acid Sponge (3).

The same method as in Example 1 was carried out except that a 4% aqueous solution of GLCA-HA produced in 1-(3) was used and that each 9.0J/cm$^2$ (measuring wavelength: 280 nm) ultraviolet ray was irradiated per side to produce a product in a sponge (hereinafter referred to as GLCN-HA Sponge (3)). The measured crosslinking ratio and isomerization ratio of this spongy product were 39.6% and 66.4%, respectively.

Preparation of Composite Sheet of Photocrosslinked-Hyaluronic Acid (1).

GLCN-HA produced in 1-(1) was dissolved in distilled water to give a concentration of 3%, the resulting aqueous solution was filled in a high-density polyethylene bag, sealed, sandwiched between two hard glass plates having a gap of 1 mm and ultraviolet ray of 10 J/cm$^2$ (measuring wavelength: 280 nm) in total was irradiated to both sides using a 800-W high-pressure mercury lamp (manufactured by Orc Seisakusho).

Then it was just frozen in an ethanol bath of −40° C. While keeping the frozen state, each of the sides thereof was irradiated with ultraviolet ray of 0.5 J/cm$^2$ (measuring wavelength: 280 nm), followed by melting to give a somewhat whitish semi-transparent product in a sheet (hereinafter referred to as GLCN-HA sheet(1)). The measured crosslinking ratio and isomerization ratio of this composite sheet were 6.0% and 68.5%, respectively. The measured breaking tenacity of the resulting composite sheet was 110.9 g.

Preparation of Composite Sheet of Photocrosslinked-Hyaluronic Acid (3).

A 4% aqueous solution of GLCN-HA produced in 1-(3) was irradiated with ultraviolet ray from a 3-kW metal halide lamp (manufactured by UshioDenki) at a dose of each 50.0 J/cm$^2$ per side whereby 100.0 J/cm$^2$ (measuring wavelength: 280 nm) for both sides and then irradiation under a frozen state was carried out in the same manner as in Example 1, except that a 800-W high-pressure mercury lamp (manufactured by Orc Seisakusho) was used at a dose of each 9.0J/cm$^2$ per side (measuring wavelength: 280 nm) whereupon a product in a sheet (hereinafter referred to as GLCN-HA Sheet (3)) was produced. The measured crosslinking ratio and isomerization ratio of this composite sheet were 48.0% and 67.3%, respectively.

Preparation of Photocrosslinked-Hyaluronic Acid Composite Film

A 4% aqueous solution of GLCN-HA prepared in the above example 1-(3) was filled in a high-density polyethylene bag, sealed, sandwiched between two hard glass plates having a gap of 1 mm and ultraviolet ray of each 5J/cm2 per side (measuring wavelength: 280 nm), in other words 10 J/cm2 in total, was irradiated to each of the sides using 800-W high-pressure mercury lamp (manufactured by Orc Seisakusho) to give a product in gel-state. Then the gel-state product was just frozen under atmosphere condition of minus 20. While keeping the frozen state, each of the sides thereof was irradiated with 0.2 J/cm2 (measuring wavelength: 280 nm) ultraviolet ray per each, in other words 0.4 J/cm$^2$ in total, using 800-W high-pressure mercury lamp. Subsequently it was thawed to give a product in a sheet.

The resulting sheet-like product was dried by placing in a constant-temperature vessel of 50, and then each of the sides thereof was irradiated again with 0.2 J/cm$^2$ (measuring wavelength: 280 nm) ultraviolet ray per each using 800-W high pressure mercury lamp to give the product in a film which was milky-white and semi-transparent.

The measured crosslinking ratio and isomerization ratio of this film-like product were 9.8% and 67.8%, respectively.

Example 2

(Preparation of Hyaluronic Acid into Which Glycidyl Thiopheneacrylate is Introduced (Hereinafter Referred to as GLTA-HA) and a Crosslinked Product Thereof Synthesis of Hyaluronic Acid into Which Glycidyl Thiopheneacrylate is Introduced (GLTA-HA)).

To 100 ml of a 1 wt % aqueous solution of hyaluronic acid (weight-average molecular weight: 800,000) were added 50 ml of water for injection and 75 ml of 1,4-dioxane, and 3 ml of glycidyl thiopheneacrylate (epoxy equivalent: 596.8) was added thereto, followed by stirring for 24 hours in a constant-temperature vessel of 50° C.

Sodium chloride (1 g) was added to the resulting solution, followed by stirring, and the mixture was poured into 800 ml of ethanol to give a cotton-like precipitate. The resulting precipitate was well washed with ethanol and dried to give 1.1 g of GLTA-HA. The measured degree of substitution of glycidyl thiopheneacrylate was 1.4%.

Preparation of Photocrosslinked-Hyaluronic Acid Gel.

A gel-state product was produced in the same manner as in the production method for a gel-state product mentioned in Example 1, except that GLTA-HA was used.

The measured rotational viscosity of 0.5 ml of the gel-state product was 246.5 Pa.s. The rotational viscosity of an aqueous solution of GLTA-HA without carrying out the ultraviolet irradiation was 90.5 Pa.s.

Preparation of Photocrosslinked-Hyaluronic Acid Film.

A water-insoluble film was produced in the same manner as in the production method for a product in a film mentioned in Example 1, except that GLTA-HA was used.

When the film which was produced by ultraviolet ray irradiation was dipped in water, it was immediately swollen and, even when it was just allowed to keep in water for one month at room temperature, the shape was still maintained. The measured breaking tenacity of this film was 76.8 g.

Preparation of Photocrosslinked-Hyaluronic Acid Sponge.

A product in a sponge by photocrosslinking GLTA-HA (hereinafter referred to as GLTA-HA) was produced in the same manner as in the production method for a product in a sponge mentioned in Example 1, except that GLTA-HA was used. The breaking tenacity of this spongy product was 92.6 g.

In the product which was melted without irradiating with ultraviolet ray after freezing, it was still in a state of solution and no change in physical property was found at all.

Preparation of Composite Sheet of Photocrosslinked-Hyaluronic Acid.

A somewhat whitish semi-transparent product in a sheet (hereinafter referred to as GLTA-HA Sheet) was produced in the same manner as in the production method for a composite sheet mentioned in Example 1, except that GLTA-HA was used. The measured breaking tenacity of this semi-transparent composite sheet was 87.8 g.

Example 3

(Preparation of Hyaluronic Acid into which Glycidyl Cinnamylideneacetate is Introduced (Hereinafter Referred to as Glcdn-HA) and a Crosslinked Product Thereof).

Synthesis of Hyaluronic Acid into which Glycidyl Cinnamylideneacetate is Introduced (Glcdn-HA).

To 100 ml of a 1 wt % aqueous solution of hyaluronic acid (weight-average molecular weight: 800,000) were added 50 ml of water for injection and 75 ml of 1,4-dioxane, and 3 ml of glycidyl cinnamylideneacetate (epoxy equivalent: 444.3) was added thereto, followed by stirring for 24 hours in a constant-temperature container of 50° C. Sodium chloride (1 g) was added to the solution, followed by stirring, and the mixture was poured into 800 ml ethanol to give a cotton-like precipitate. The resulting precipitate was well washed with ethanol and dried to give 1.1 g of GLCdN-HA. The measured degree of substitution of glycidyl cinnamylideneacetate was 3.1%.

Preparation of Photocrosslinked-Hyaluronic Acid Gel.

A gel-state product was produced in the same manner as in the production method for a gel-state product mentioned in Example 1, except that GLCdN-HA was used.

The measured rotational viscosity of 0.5 ml of the gel-state product was 220.0 Pa.s. The rotational viscosity of an aqueous solution of GLCdN-HA without carrying out the ultraviolet irradiation was 61.0 Pa.s.

Preparation of Photocrosslinked-Hyaluronic Acid Film.

A water-insoluble film was produced in the same manner as in the method for a product in a film mentioned in Example 1, except that GLCdN-HA was used.

When the film which was produced with ultraviolet ray irradiation was dipped in water, it was immediately swollen and, even when it was just allowed to keep in water for one month at room temperature, the shape was still maintained.

The measured breaking tenacity of this film was 23.6 g.

Preparation of Photocrosslinked-Hyaluronic Acid Sponge.

A product in a sponge (hereinafter referred to as GLCdN-HA Sponge) was produced in the same manner as in the production method for a product in a sponge mentioned in Example 1, except that GLCdN-HA was used. The measured breaking tenacity of this spongy product was 70.3 g.

In the product which was melted without irradiating with ultraviolet ray after freezing, it was still in a state of solution and no change in physical property was found at all.

Preparation of Composite Sheet of Photocrosslinked-Hyaluronic Acid.

A somewhat whitish semi-transparent product in a sheet (hereinafter referred to as GLCdN-HA Sheet) was produced in the same manner as in the production method for a composite sheet mentioned in Example 1, except that GLCdN-HA was used.

The measured breaking tenacity of this semi-transparent composite sheet was 102.2 g.

Example 4

(Preparation of Hyaluronic Acid into which Glycidyl Sorbate is Introduced (Hereinafter Referred to as GLSR-HA) and a Crosslinked Product Thereof).

Synthesis of Hyaluronic Acid into which Glycidyl Sorbate is Introduced (GLSR-HA).

To 100 ml of a 1 wt % aqueous solution of hyaluronic acid (weight-average molecular weight: 800,000) were added 50 ml of water for injection and 75 ml of 1,4-dioxane, and 3 ml of glycidyl sorbate (epoxy equivalent: 367.4) was added thereto, followed by stirring for 24 hours in a constant-temperature container of 50° C.

Sodium chloride (1 g) was added to the solution, followed by stirring, and the mixture was poured into 800 ml of ethanol to give a cotton-like precipitate. The resulting precipitate was well washed with ethanol and dried to give 1.1 g of GLSR-HA. The measured degree of substitution of glycidyl sorbate was 1.7%.

Preparation of Photocrosslinked-Hyaluronic Acid Gel.

A gel-state product was produced in the same manner as in the production method for a gel-state product mentioned in Example 1, except that GLSR-HA was used.

The measured rotational viscosity of 1.0 ml of the gel-state product was 51.8 Pa.s. The rotational viscosity of an aqueous solution of GLSR-HA without carrying out the ultraviolet irradiation was 31.1 Pa.s.

Preparation of Photocrosslinked-Hyaluronic Acid Film.

A water-insoluble product in a film was produced in the same manner as in the production method for a product in a film mentioned in Example 1, except that GLSR-HA was used. The measured breaking tenacity of this film was 68.9 g.

When the film which was produced with ultraviolet ray irradiation was dipped in water, it was immediately swollen and, even when it was just allowed to keep in water for one month at room temperature, the shape was still maintained.

Preparation of Photocrosslinked-Hyaluronic Acid Sponge.

A product in a sponge (hereinafter referred to as GLSR-HA Sponge) was produced in the same manner as in the production method for a product in a sponge mentioned in Example 1, except that GLSR-HA was used. The measured breaking tenacity of this spongy substance was 35.5 g.

In the product which was melted without irradiating with ultraviolet ray after freezing, it was still in a state of solution and no change in physical property was found at all.

Preparation of Composite Sheet of Photocrosslinked-Hyaluronic Acid.

A somewhat whitish semi-transparent product in a sheet (hereinafter referred to as GLSR-HA Sheet) was produced in the same manner as in the production method for a composite sheet mentioned in Example 1, except that GLSR-HA was used.

Reference Example 2

(Preparation of Hyaluronic Acid into which Aminopropyl Cinnamate is Introduced (Hereinafter Referred to as 3APC-HA) and a Crosslinked Product Thereof).

Preparation of Hyaluronic Acid into which Aminopropyl Cinnamate is Introduced (3APC-HA).

Preparation was carried out according to a method mentioned in JP-A-2002-249501. Thus, to 100 ml of a 1 wt % aqueous solution of hyaluronic acid (weight-average molecular weight: 800,000) were added 50 ml of distilled water and 75 ml of 1,4-dioxane, then 172 mg of N-hydroxysuccinimide (HOSu), 143 mg of 1-ethyl-3-(3-dimethylaminopropyl)carbodiimide hydrochloride (EDCl.HCl) and 181 mg of aminopropyl cinnamate hydrochloride (HCl.H$_2$N(CH$_2$)$_3$OCO—CH=CH—Ph in which —Ph is phenyl) were sequentially added thereto, the mixture was allowed to react at room temperature for 3 hours, 0.5 g of sodium hydrogen carbonate was added thereto, followed by stirring for all day and night, 6 g of sodium chloride was added thereto and 400 ml of ethanol was poured into the reaction solution to separate a precipitate. The precipitate was recovered by washing with 80% ethanol twice and dried at 40° C. in vacuo to give 1.0 g of 3APC-HA. The measured degree of substitution of aminopropyl cinnamate was 8.2%.

Preparation of Photocured-3APC-HA Sponge.

An aqueous solution in which 3APC-HA was dissolved in distilled water to give a concentration of 3% was filled in a high-density polyethylene bag, sealed, sandwiched between two hard glass plates having a space of 1 mm and frozen in an ethanol bath of −40° C. While keeping the frozen state, ultraviolet ray was irradiated to both sides thereof at a dose of 2.0 J/cm$^2$ (measured wavelength: 280 nm) per side and fused to give a product in a sponge (hereinafter referred to as 3APC-HA Sponge). The crosslinking ratio of the photocured-3APC-HA sponge was 32.8%.

The measured breaking tenacity of this spongy product was 157.8 g.

Preparation of Composite Sheet of Photocured-3APC-HA.

An aqueous solution in which 3APC-HA was dissolved in distilled water to give a concentration of 3% was filled in a high-density polyethylene bag, sealed, sandwiched between two hard glass plates having a space of 1 mm and irradiated to both sides thereof with each 5.0 J/cm$^2$ ultraviolet ray (measuring wavelength: 280 nm) per side.

Then, it was frozen in an ethanol bath of −40° C. and, while keeping the frozen state, ultraviolet ray was irradiated to both sides at each dose of 0.5 J/cm$^2$ per side (measured wavelength: 280 nm), followed by fusing to give a somewhat whitish semi-transparent product in a sheet (hereinafter referred to as 3APC-HA Sheet).

The crosslinking ratio of the composite sheet of photocured-3APC-HA was 5.8%.

The measured breaking tenacity of this semi-transparent composite sheet was 181.7 g.

Reference Example 3

(Preparation of Diglycidyl Ether Crosslinking Hyaluronic Acid Sponge).

Preparation was carried out according to a method mentioned in JP-A-2002-233542. Thus, to 100 ml of a 1 wt % aqueous solution of hyaluronic acid (weight-average molecular weight: 800,000) was added 1 ml of diglycidyl ether (trade name: Denacol EX-303; Nagase Kasei Kogyo), the resulting solution was flown into a container made of polypropylene so as to give a liquid thickness of about 2 mm and allowed to stand for reaction in a constant-temperature vessel of 50° C. for 9 hours and the reaction solution was quickly frozen in a freezer of −80° C. and freeze-dried at 10 Pa. Then, the resulting diglycidyl ether crosslinking hyaluronic acid sponge was washed very well with water for injection in a sufficient amount. The product was freeze-dried once again to give diglycidyl ether crosslinking hyaluronic acid sponge (hereinafter referred to as DGLE-HA Sponge).

Example 5

(Investigation on Degradability).

Each of the photocrosslinked-polysaccharide products of Examples 1 to 4, and Reference Example 2, were tested. Three sheets in a size of 2 cm×1 cm and 1 mm thickness were prepared for each of the photocrosslinked-polysaccharides (identified in FIG. 2). The sheets were stirred in 0.5N aqueous solution of NaOH. The time required for saponification of the sheets was measured and the degradability of the sheets was compared. The results are shown in FIG. 2, where the horizontal bars identify the mean values for time and the lines ending with a T-shape, represent the standard deviation for the time.

Judgment was visually carried out and the point in time when no solid was found in the 0.5N aqueous solution of NaOH was defined as a termination time.

Figure 2:
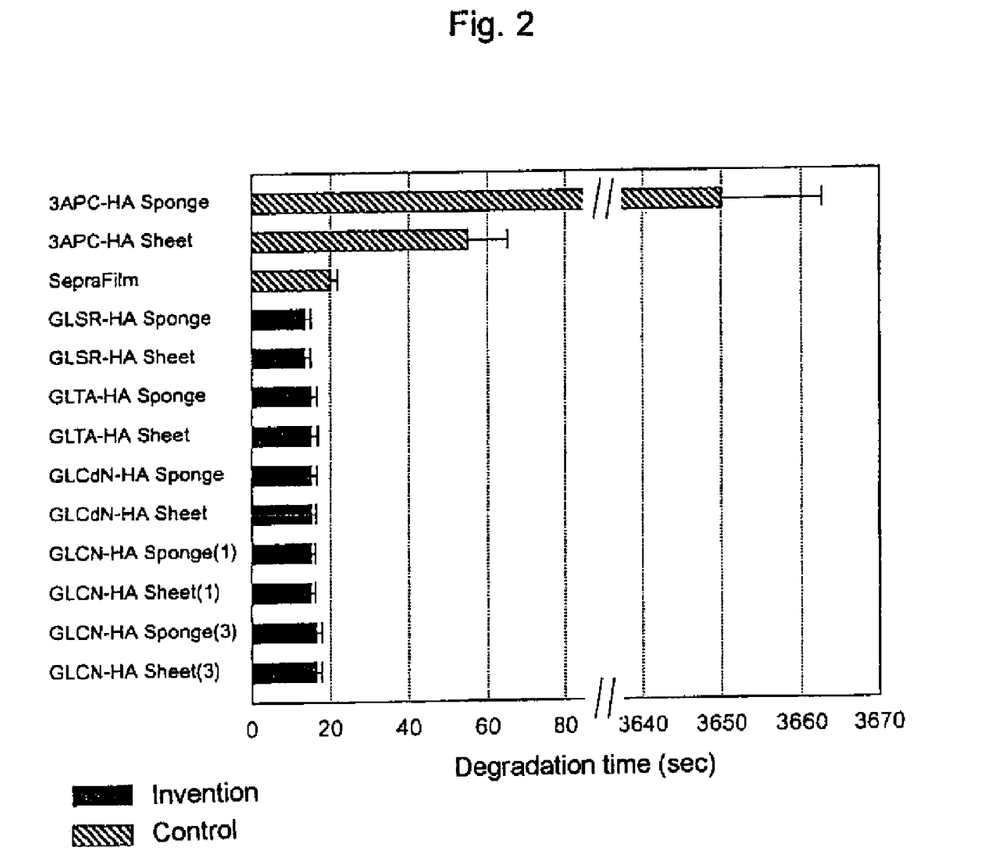
FIG. 2 shows the result of investigation of degradability for the composite sheet of the photocrosslinked-polysaccharide and the photocrosslinked-polysaccharide sponge in Example 5.

In FIG. 2, "GLCN-HA" is hyaluronic acid into which glycidyl cinnamate was introduced, "GLCdN-HA" is hyaluronic acid into which glycidyl cinnamylideneacetate was introduced, "GLTA-HA" is hyaluronic acid into which glycidyl thiopheneacrylate was introduced, "GLSR-HA" is hyaluronic acid into which glycidyl sorbate was introduced and "3APC-HA" is hyaluronic acid into which aminopropyl cinnamate was introduced. "Sheet" means a composite sheet of this present invention and "Sponge" means a product in a sponge of this present invention.

As a control, SepraFilm™ (manufactured by Genzyme; sold by Kaken Seiyaku) was used.

It was confirmed from FIG. 2 that in 3APC-HA nearly one hour was required for alkali saponification in a sponge and 57 seconds were required for disappearance even in a composite sheet while, in GLCN-HA, it disappeared within 15 seconds regardless of its form.

In GLCN-HA (GLCN-HA Sponge (3) and GLCN-HA Sheet (3)) in which the degree of substitution and the crosslinking ratio were enhanced, all of them disappeared within 17 seconds regardless of its forms of sponge and composite sheet. It has been known that, in general, the degradability lowers when degree of substitution and the crosslinking ratio become high but, in the present invention, it has been confirmed that excellent degradability is constantly available regardless of the degree of substitution and the crosslinking ratio.

duced (3APC-HA sheet), no adhesion was found in all of the three cases but the composite sheet remained by firmly keeping its form.

In the case of the sponge of photocrosslinked-hyaluronic acid into which glycidyl cinnamate was introduced (GLCN-HA Sponge(1)), no adhesion was found in all of the eleven cases. In addition, the sponge completely disappeared and, further, no abnormality was found in liver and in other organs.

In the case of the sponge of photocrosslinked-hyaluronic acid into which aminopropyl cinnamate was introduced (3APC-HA sponge), it remained in a resinous state in milky white color in all of the two cases whereupon a severe adhesion to wound took place.

In the case of the diglycidyl ether crosslinking hyaluronic acid sponge (DGLE-HA sponge), adhesion was found in all of the two cases. Although the sponge itself completely disappeared, the surrounding area of the liver became thick and the turbidity within a wide range was found.

As mentioned above, in the 3APC-HA sponge, severe adhesion was found, while, in the GLCN-HA sponge, a preventive effect for adhesion was found in all cases. That is presumably due to the fact that degradability of the GLCN-HA sponge is superior to 3APC-HA sponge.

TABLE 1

| Photoreactive polysaccharide | | GLCN-HA | 3APC-HA | DGLE-HA |
|---|---|---|---|---|
| photocrosslinked-polysaccharide composite sheet | Degradability | disappeared | Remained | |
| | Adhesion preventive effect | adhesion prevented | Adhesion prevented | |
| | Observations in organs | No abnormality | No abnormality | |
| photocrosslinked-polysaccharide sponge | Degradability | disappeared | Remained | Disappeared |
| | Adhesion preventive effect | adhesion prevented | Severely adhered | Adhered |
| | Observations in organs | No abnormality | No abnormality | liver became turbid |

Example 6

(Investigation in Degradability In Vivo).

The adhesion preventive effect and the degradability were investigated using the following rat in which the abdominal wall was deficient and the cecum was abraded.

After the secum side of rat was lightly abraded for several times, a deficient area of 30×40 mm was formed at the abdominal sidewall and was covered by the photo-crosslinked-polysaccharide product mentioned in Table 1 in a size of 4 cm×5 cm×0.3 mm. After 7 days, it was dissected and the state whether there was adhesion between abdomen and cecum and whether there was residue of each photo-crosslinked-polysaccharide product was judged whereupon adhesion preventive effect and degradability were investigated. The result is shown in the following Table 1.

Each of the photocrosslinked-polysaccharide products was produced in Example 1, Reference Example 2 and Reference Example 3. In addition GLCN-HA Sponge (1) and GLCN-HA Sheet (1) were used as the GLCN-HA.

As a result of the test, in the case of the composite sheet of photocrosslinked hyaluronic acid into which glycidyl cinnamate was introduced (GLCN-HA Sheet (1)), no adhesion was found in all of the three cases. In addition, the composite sheet completely disappeared and, further, no abnormality was found in liver and in other organs.

In the case of the composite sheet of photocrosslinked hyaluronic acid into which aminopropyl cinnamate was intro- Example 7

(Investigation in Adhesion Preventive Effect In Vivo).

A rabbit in which the intestinal tract was adhered was used for comparison of adhesion preventive effect of SepraFilm™ (manufactured by Genzyme; sold by Kaken Seiyaku) with the photocrosslinked-polysaccharide composite sheet according to the present invention.

1. Preparation of a Rabbit Having Primary Adhesion of Intestinal Tract.

Three Japanese White Rabbits (male; about 20 week-old; body weight: ca. 3 kg) was used. Laparotomy was carried out under anesthetizing by inhalation of halothane (Forane; Takeda Chemical Industries) and surface of jejunum was abraded for 30 times with gauze at a constant rate. Then surface of ileum adjacent to the abraded jejunum was abraded similarly. The abraded range was 15 mm width and 30 mm length (area: 450 $mm^2$). Then, the both abraded sites were covered with sanitary cotton impregnated with iodine tincture (3% iodine and 2% potassium iodide). After 7 minutes, the sanitary cotton was removed, the sites were dried for 3 minutes and then abdominal wall and skin were sutured to prepare the rabbit having primary adhesion. By such an operation, adhesion could be formed between the jejunum and the ileum.

2. Exfoliation of Primary Adhesion in Intestinal Tract and Administration of a Substance to be Tested (Preparation of Model for Evaluation).

After preparation of a rabbit having primary adhesion, each rabbit was once subjected to laparotomy to observe the degree of adhesion. And individuals in which severe adhesion accompanied by formation of thin film was found, were selected.

The adhered site was exfoliated under a microscope for operation and, after the area of the site wherefrom the adhesion was removed was measured, GLCN-HA Sheet (1) (the same one that was used in Example 6) and SepraFilm™ were administered as substances to be tested. Each of the products to be tested was cut in an area which was larger, to an extent of 20%, than the area of the site wherefrom the adhesion was exfoliated and attached to the site wherefrom the adhesion was exfoliated. Nothing was administered to a control group. After administration of the products to be tested, abdominal wall and skin were sutured to finish the preparation of the model for evaluation.

3. Evaluation of Preventive Ability for Adhesion.

After 2 weeks from the preparation of the models for evaluation, laparotomy was carried out to observe whether re-adhesion took place. When re-adhesion took place, its area was measured. Incidentally, adhesion was scored in four stages: 0 for no adhesion; 1 for weak adhesion; 2 for medium adhesion; and 3 for strong adhesion.

4. Result.

In the control group, there was strong re-adhesion where the score 3 was found. As compared with the primary adhesion area which was 350 mm$^2$, the re-adhered area was 1,200 mm$^2$ whereby the re-adhesion rate was 342.9%.

In the case of GLNC-HA Sheet (1), as compared with the primary adhesion area which was 1,900 mm$^2$, no re-adhesion was found at all whereby the score was 0. Re-adhered area was 0 mm$^2$ and re-adhesion rate was 0%.

On the other hand, in the case of SepraFilm™, adhesion in a medium degree where the score 2 was found and, as compared with the primary adhesion area which was 750 mm$^2$, the re-adhered area was 1,335 mm$^2$ whereby the re-adhesion rate was 178.0%.

From the above, it is apparent that GLCN-HA Sheet shows a more excellent preventive action for adhesion than Sepra-Film™.

Example 8

(Investigation of Adhesive Preventive Ability Using a Rat Uterine Horn Model).

Since it has been known that a rat uterine horn model shows more severe adhesion than a rabbit intestinal re-adhesion model, further adhesion preventive property was investigated using such a model.

1. Preparation of the Model.

As the rat, Crj:SD strain (SPF.) female rat (7 week-old) was used and, after subjecting to a preliminary breeding for one week before the test, it was used in the present test.

Hairs on abdomen of the rat were cut under anesthetizing with Nembutal. A median incision of about 4 cm was made and (a) the right abdominal wall of the rat was cut to the muscular layer using an ophthalmologic trepan and the muscular layer was exfoliated using a pair of tweezers. Then, the uterine horn was exposed, and (b) a transverse incision was carried out at 4 places with an interval of 2 to 3 mm from the site which was about 1 cm to the uterine cervix from the ovary. Bleeding from the wound was appropriately stopped by an electric knife. The site (c) which was about 3 to 4 mm from the end of the transversely incised uterine horn and the site which was about 3 to 4 mm from the end of the area where the abdominal wall was deficient were subjected to a one-needle sewing with a yarn of 8/0 whereupon the wounds prepared in (a) and (b) were made closer.

2. Administration of Products to be Tested.

Between the area where the abdominal wall was deficient and the wounded area of uterine horn, GLCN-HA Sheet (3) and SepraFilm™ in a size of 2.0 cm×1.0 cm were inserted and they were used as test groups. Each group consists of 10 rats.

3. Evaluation.

The evaluation is carried out as follows. Specifically, after 7 days from embedding, the rats were killed by depletion from the carotid artery under anesthetizing with ether and subjected to anatomy and the site where adhesion was generated was evaluated by the following scoring system depending on the degree of adhesion: 0—no adhesion; 1—light adhesion, easily exfoliated; 2—medium adhesion, exfoliation possible; and, 3—severe adhesion; exfoliation impossible.

4. Results.

Results of the judgments are shown in Table 2 below.

TABLE 2

| Score | GLCN-HA Sheet (3) | SepraFilm ™ |
|---|---|---|
| 0 | 8 | 0 |
| 1 | 2 | 7 |
| 2 | 0 | 3 |
| 3 | 0 | 0 |
| Adhesion-Prevention Score | 8/10 | 0/10 |

In the present models for adhesion, adhesion was found in all of the ten rats in the case of SepraFilm™ whereby no effect was found at all while, in the case of GLCN-HA Sheet (3) according to the present invention, adhesion was prevented in 8 rats among the ten rats.

From the above result, it has been made clear that GLCN-HA Sheet has a sufficient preventive effect for adhesion.

While the invention has been described in detail and with reference to specific embodiments thereof, it will be apparent to one skill in the art that various changes and modifications can be made to the disclosures made herein without departing from the spirit and scope of the invention.

This application is based on Japanese Application No. 2004-268145 filed on Sep. 15, 2004, the entire contents of which are incorporated hereinto by reference. All other references cited herein are incorporated in their entirety.

INDUSTRIAL APPLICABILITY

The present invention provides a photocrosslinked-polysaccharide as a photocrosslinked-product produced by crosslinking a photoreactive polysaccharide in which a glycidyl ester of a photoreactive compound having a carboxyl group and an unsaturated carbon double bond in a molecule is bound to a polysaccharide. Various forms for a photo-crosslinked-product can be provided. The photocrosslinked-polysaccharide exhibits excellent strength and biodegradability, moreover the excellent characteristics of the conventional photocrosslinked-glycosaminoglycan gel and sponge still remain in the photocrosslinked-polysaccharide. The photo-crosslinked-polysaccharide of the present invention can be used in medical products, particularly an antiadhesive agent after operation, a substrate for sustained-release of drug or a substrate for culturing cells.

What is claimed is:

1. A photoreactive polysaccharide comprising:
a polysaccharide covalently bonded to a glycidyl ester represented by the formula (1) by opening the epoxy group:

(1)

wherein represents a residue of a photoreactive compound having the carboxyl group identified, and an unsaturated carbon double bond;
and wherein the polysaccharide is a hyaluronic acid; and, a photoreactive compound is selected from the group consisting of: cinnamic acid, thiopheneacrylic acid and cinnamilideneacetic acid.

2. The photoreactive polysaccharide according to claim 1, wherein the photoreactive compound is cinnamic acid.

3. The photoreactive polysaccharide of claim 1 wherein the polysaccharide is covalently bonded to the glycidyl ester by an ester bond to a carboxyl group of the polysaccharide.

4. A photocrosslinked-polysaccharide produced by crosslinking the photoreactive polysaccharide according to claim 1.

5. A photocrosslinked-polysaccharide produced by crosslinking the photoreactive polysaccharide according to claim 2.

6. A photocrosslinked-polysaccharide produced by crosslinking the photoreactive polysaccharide according to claim 3.

7. A photocrosslinked-polysaccharide in a gel state produced by irradiating a solution of the photoreactive polysaccharide according to claims 1 with light.

8. A photocrosslinked-polysaccharide in a sponge state produced by freezing or freeze-drying a solution of the photoreactive polysaccharide according to claim 1, and irradiating the resulting frozen solution or freeze-dried product with light.

9. A photocrosslinked-polysaccharide having both properties of a gel-state product and a sponge-state product produced by: (a) irradiating a solution of the photoreactive polysaccharide according to claim 1 with light to obtain a gel-state product; freezing the gel-state product; and, irradiating the frozen gel-state product with light while keeping the frozen state; or, (b) irradiating a solution of the photoreactive polysaccharide according to claim 1 with light to obtain a gel-state product; freeze-drying the gel-state product; and, irradiating the freeze-dried gel state product with light.

10. A photocrosslinked-polysaccharide in the state of a film produced by drying a solution of the photoreactive polysaccharide according to claim 1 to obtain a film thereof, and irradiating the film with light.

11. A photocrosslinked-polysaccharide produced by the steps comprising:
irradiating a solution of the photoreactive polysaccharide according to claim 1 with light to obtain a gel-state product;
freezing the gel-state product;
irradiating the frozen gel-state product with light while keeping the frozen state to obtain a composition with both properties of gel-state product and sponge-state product; and,
drying the composition, and irradiating the composition thus dried with light.

12. A medical product which comprises the photocrosslinked-polysaccharide according to any one of claims 4 to 11.

13. The medical product according to claim 12, which is an antiadhesive agent.

14. The medical product according to claim 12, which is a substrate for sustained drug release.

15. The medical product according to claim 12, which is a substrate for culturing cells.

* * * * *